United States Patent
Potasek et al.

(10) Patent No.: US 10,273,149 B2
(45) Date of Patent: Apr. 30, 2019

(54) GAS DETECTOR WITH A THERMALLY UNIFORM MEMS DIE

(71) Applicant: Carrier Corporation, Farmington, CT (US)

(72) Inventors: David P. Potasek, Lakeville, MN (US); John Carl Christenson, Prior Lake, MN (US); Marcus Allen Childress, Farmington, MN (US)

(73) Assignee: CARRIER CORPORATION, Farmington, CT (US)

( * ) Notice: Subject to any disclaimer, the term of this patent is extended or adjusted under 35 U.S.C. 154(b) by 0 days.

(21) Appl. No.: 15/222,754

(22) Filed: Jul. 28, 2016

(65) Prior Publication Data

US 2017/0029270 A1 Feb. 2, 2017

Related U.S. Application Data

(60) Provisional application No. 62/197,924, filed on Jul. 28, 2015.

(51) Int. Cl.
*B81B 7/00* (2006.01)
*G01N 27/12* (2006.01)

(52) U.S. Cl.
CPC .......... *B81B 7/0096* (2013.01); *B81B 7/0087* (2013.01); *G01N 27/128* (2013.01); *B81B 2201/0214* (2013.01)

(58) Field of Classification Search
CPC ......... G01N 27/128; G01N 2021/0346; G01N 2021/058; G01N 2021/651; G01N 21/05; G01N 21/65; G01N 21/658; G01N 27/02; G01N 27/14; G01N 27/16; G01N 33/0036; B81B 2201/0214; B81B 7/0087; B81B 7/0096

USPC .......................................... 422/95; 73/204.11
See application file for complete search history.

(56) References Cited

U.S. PATENT DOCUMENTS

| | | | |
|---|---|---|---|
| 6,399,177 B1 * | 6/2002 | Fonash | B81C 1/00047 428/119 |
| 6,596,236 B2 * | 7/2003 | DiMeo, Jr. | G01N 21/59 422/88 |
| 6,732,567 B2 * | 5/2004 | Briscoe | F04B 19/006 73/23.2 |
| 7,282,393 B2 | 10/2007 | Tarn | |

(Continued)

FOREIGN PATENT DOCUMENTS

| CN | 103675048 A | 3/2014 | |
|---|---|---|---|
| EP | 3124963 A1 * | 2/2017 | G01N 27/128 |

(Continued)

OTHER PUBLICATIONS

Bhattacharyya; "Technological Journey Towards Reliable Microheater Development for MEMS Gas Sensors: A Review"; IEEE Transactions on Device and Materials Reliability 14(2); Jun. 2014; 1 page (Abstract Only).

(Continued)

*Primary Examiner* — Edward Chin
(74) *Attorney, Agent, or Firm* — Cantor Colburn LLP

(57) ABSTRACT

A microelectromechanical systems die including a thermally conductive substrate, at least one insulator film disposed on the thermally conductive substrate, a sensor material disposed on the at least one insulator film, and a heater circumferentially disposed around the sensor material.

27 Claims, 5 Drawing Sheets

(56) References Cited

U.S. PATENT DOCUMENTS

| | | |
|---|---|---|
| 8,736,000 B1 | 5/2014 | Manginell et al. |
| 8,801,917 B2 | 8/2014 | Merz et al. |
| 2007/0113642 A1* | 5/2007 | Bonne .................. G01F 1/6845 73/204.11 |
| 2007/0212263 A1* | 9/2007 | Shin ...................... G01N 27/16 422/95 |
| 2011/0138882 A1 | 6/2011 | Moon et al. |
| 2012/0085750 A1 | 4/2012 | Hauer |
| 2012/0193730 A1 | 8/2012 | Imamura et al. |
| 2017/0097314 A1* | 4/2017 | Christenson .............. B81B 7/02 |

FOREIGN PATENT DOCUMENTS

| | | |
|---|---|---|
| JP | 2009058389 A | 3/2009 |
| WO | 2014012948 A1 | 1/2014 |

OTHER PUBLICATIONS

EP Extended Search Report; Application No. EP 16181663.2; dated Jan. 4, 2017; 8 pages.

Hwang et al.; "Development of Micro-Heaters with Optimized Temperature Compensation Design for Gas Sensors"; Open Access Sensors 2011; ISSN 1424-8220; 12 pages.

Wiche et al.; "Metalloxid-Gassensoren mit Siliziumcarbid Micro-Hotplate"; Jan. 4, 2008; Retrieved from URL: https://depositonce.tu-berlin.de/bitstream/11303/2036/2/Dokument_50.pdf; 156 pages.

Wiche et al.; "Thermal analysis of silicon carbide based micro hotplates for metal oxide gas sensors"; Sensors and Actuators A: Physical, vol. 123-124; Sep. 23, 2005; 1 Page (Abstract Only).

\* cited by examiner

GAS DETECTOR WITH A THERMALLY UNIFORM MEMS DIE

CROSS-REFERENCE TO RELATED APPLICATIONS

The present application is a nonprovisional patent application, which claims priority to U.S. Provisional Patent Application Ser. No. 62/197,924, filed Jul. 28, 2015, and having the title "GAS DETECTOR WITH A THERMALLY UNIFORM MEMS DIE," which is herein incorporated in its entirety.

TECHNICAL FIELD OF THE DISCLOSED EMBODIMENTS

The present embodiments are generally related to the art of microelectromechanical (MEMS) devices, and more particularly, to a gas detector with a thermally uniform MEMS die.

BACKGROUND OF THE DISCLOSED EMBODIMENTS

Generally, gas detector devices include a substrate, often made of ceramic, a sensing film, a central heater. To operate the gas detector device, the gas detector may utilize surface adsorption on the sensing film to cause changes in resistance of the sensing film as a function of varying concentrations of different gases. In order to restrict these resistive changes to a single gas species, the central heater must hold the sensing film to a constant and uniform temperature.

While it is possible for the central heater to heat the die to the required temperature, thermal gradients develop on the sensing surface due, in part, to necessary structures which are proximal to the sensing film that contribute significant conductive and convective heat transfer from portions of the device. This produces non-uniform performance of the detector and may cause the detector to become sensitive to non-target chemicals.

Because a gas detector device often operates at high temperatures and under an electrical bias, migration of portions of its metal components may occur. Displaced metals may cause electrical shorts or undesirable changes in electrical properties of the device.

Accordingly, there exists a need for a MEMS die to improve performance of a gas detector.

SUMMARY OF THE DISCLOSED EMBODIMENTS

In one aspect, a gas detector device is provided. The gas detector device includes a microelectromechanical systems (MEMS) die, and sensor material disposed on the MEMS die. The MEMS die includes a thermally conductive substrate and at least one insulator film disposed over the thermally conductive substrate. In an embodiment, the thermally conductive substrate is composed of silicon. In one embodiment, the sensing material is substantially centered on the at least one insulator film.

The MEMS die includes at least one electrode in contact with the sensor material. The MEMS die further includes a temperature sensor disposed around the sensor material. In an embodiment, the temperature sensor is circumferentially disposed around the sensor material. In another embodiment, the temperature sensor surrounds three sides of the sensor material.

The MEMS die further includes a heater circumferentially disposed around the sensor material, and temperature sensor. In an embodiment, the heater includes a line width dimension, wherein the linewidth dimension is less than or equal to approximately 100 micrometers.

In an embodiment, the MEMS die further includes at least one aperture disposed within the at least one insulator film. In another embodiment, MEMS die further includes at least one passive heat exchanger operably coupled to at least one bond pad, the at least one bond pad is disposed on the at least one insulator film surface.

In one embodiment, the at least one passive heat exchanger is located on a periphery of the at least one insulator film surface. In an embodiment, the at least one passive heat exchanger and the at least one bond pad are disposed within the aperture. In some embodiments, the passive heat exchangers are coupled to place the MEMS die in a spider die (i.e. floating die) configuration.

DETAILED DESCRIPTION OF THE DISCLOSED EMBODIMENTS

Figure 1:
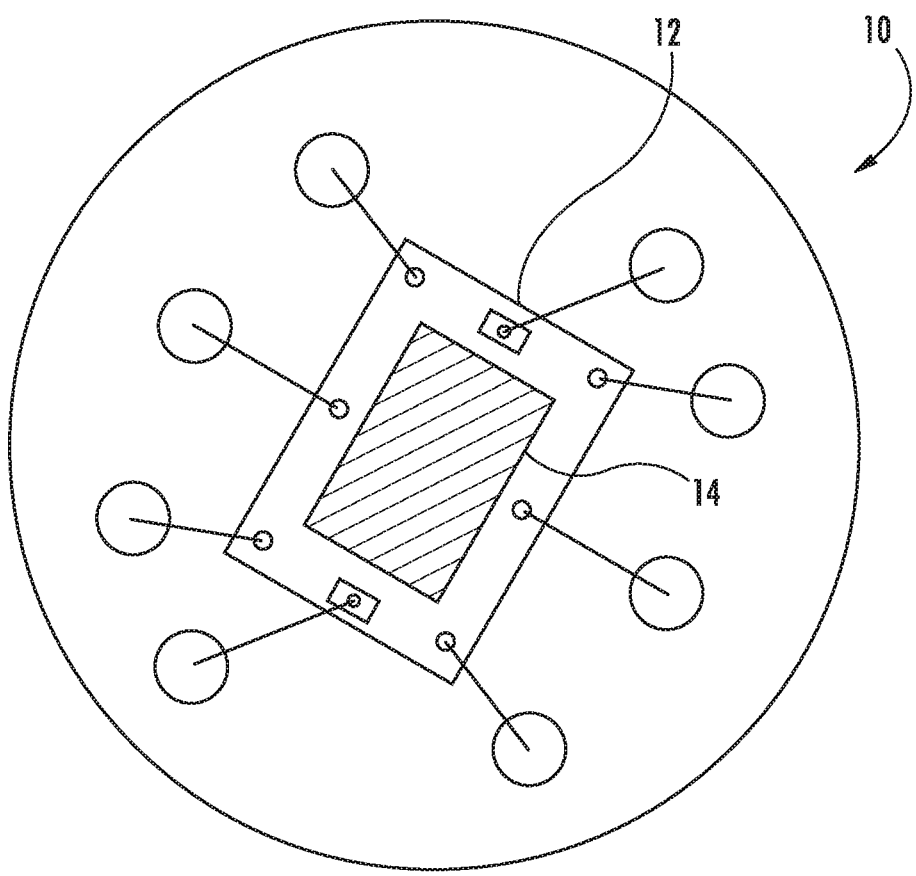
FIG. 1 illustrates a schematic drawing of gas detector sensor according to one embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

FIG. 1 illustrates an embodiment of a gas detector device, generally indicated at 10. The gas detector device 10 includes a microelectromechanical systems (MEMS) die 12, and sensor material 14 disposed on the MEMS die 12. The sensor material 14 is configured to detect the presence of a target gas as it passes over the sensor material 14. For example, the gas detector device 10 may be constructed and arranged to detect hydrogen sulfide or any other known target gas.

Figure 2:
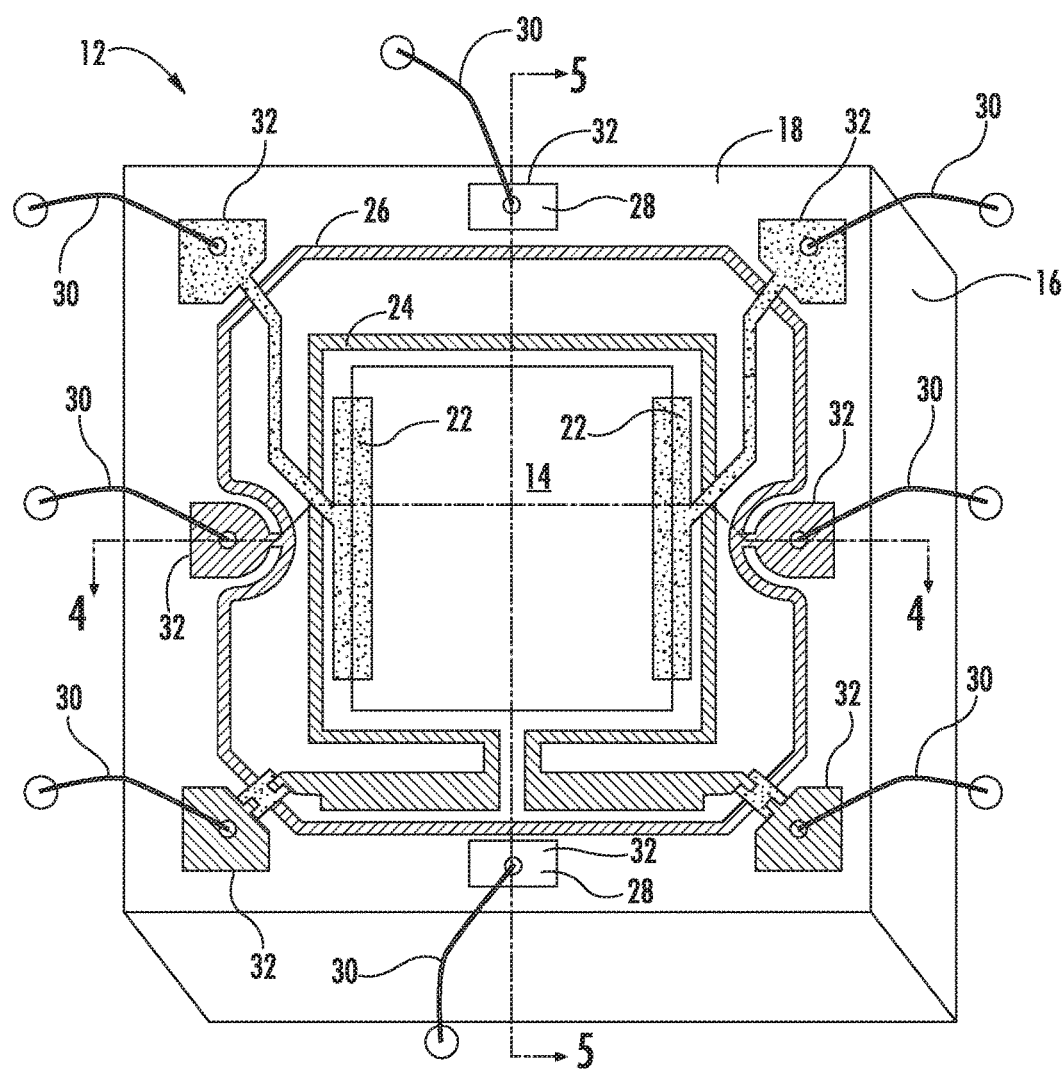
FIG. 2 illustrates a perspective view of a microelectromechanical systems die according to one embodiment of the present disclosure.
Figure 3:
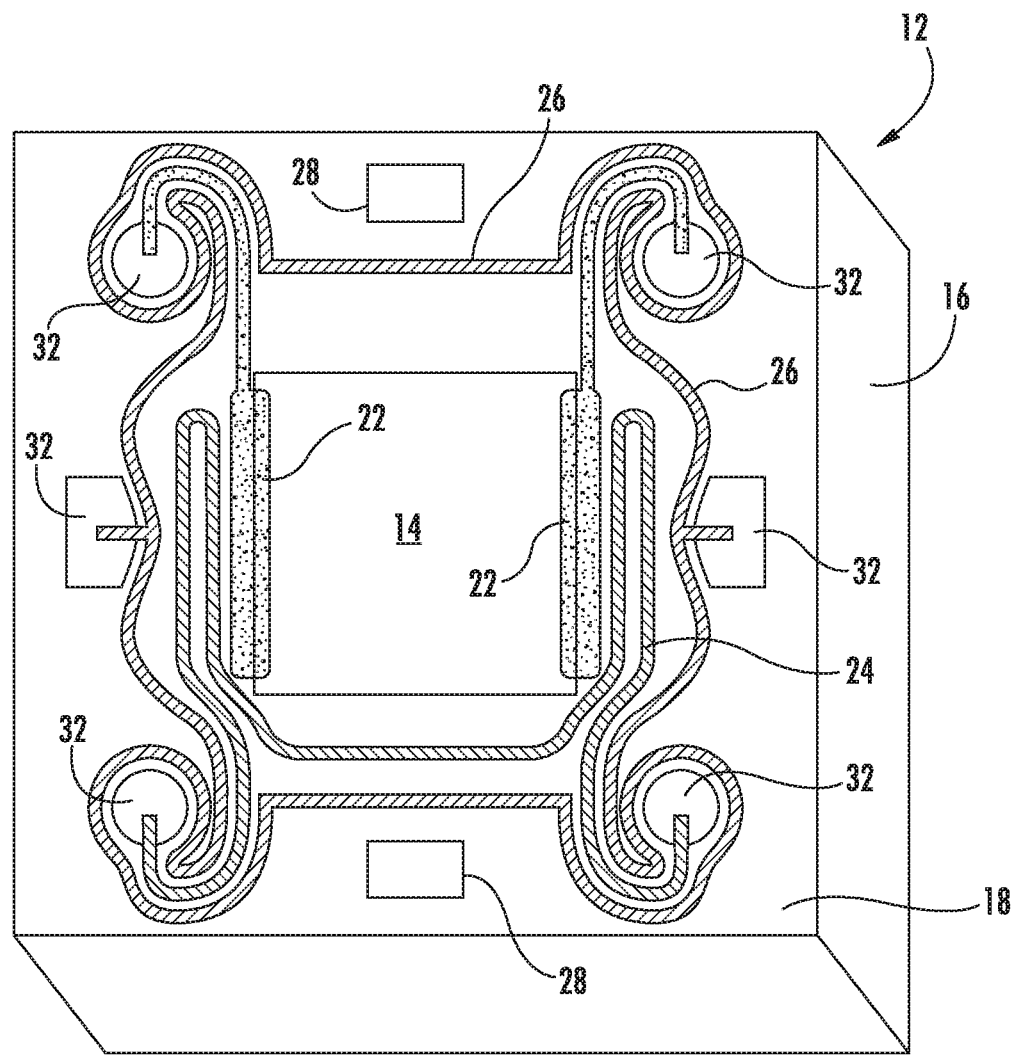
FIG. 3 illustrates a perspective view of a microelectromechanical systems die according to one embodiment of the present disclosure.

With reference to FIGS. 2 and 3, the MEMS die 12 includes a thermally conductive substrate 16 and at least one insulator film 18 (shown in FIGS. 4-6) disposed over the thermally conductive substrate 16. In an embodiment, the thermally conductive substrate 16 is composed of silicon. In one embodiment, the sensing material 14 is substantially centered on the at least one insulator film 18.

Figure 4:
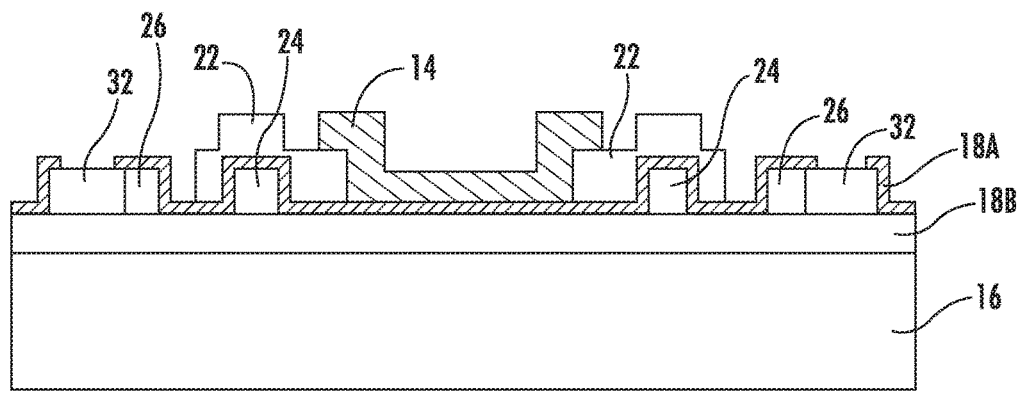
FIG. 4 illustrates a cross-sectional view of a microelectromechanical systems die according to one embodiment of the present disclosure.
Figure 5:
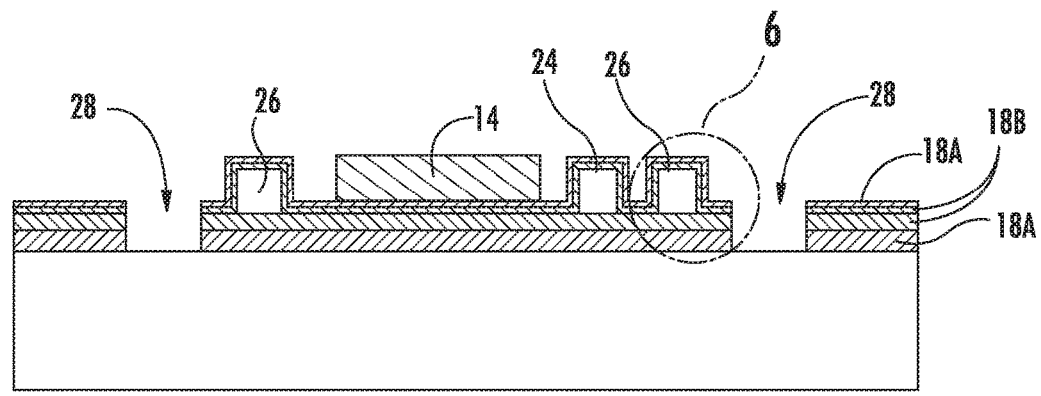
FIG. 5 illustrates a cross-sectional view of a microelectromechanical systems die according to one embodiment of the present disclosure.
Figure 6:
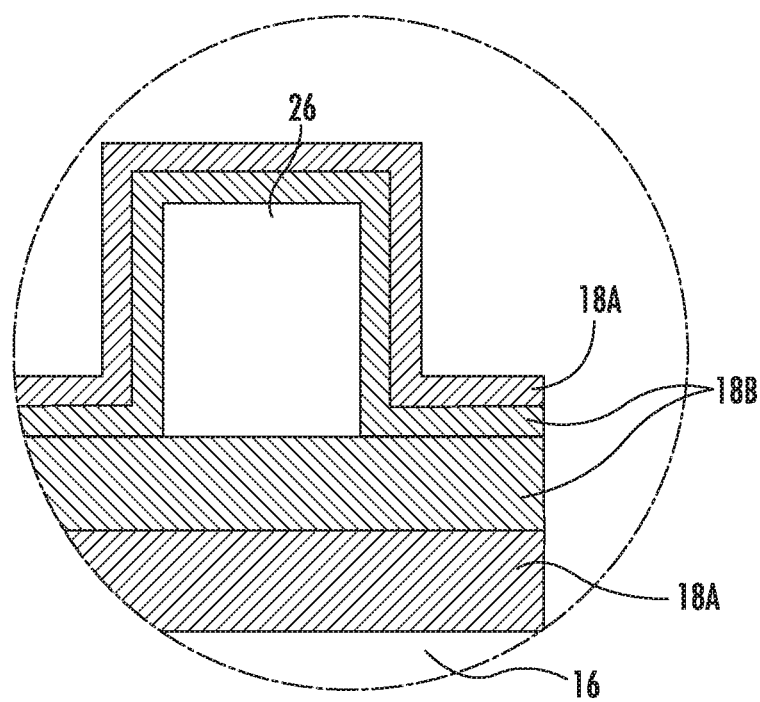
FIG. 6 illustrates a cross-sectional view of an insulator stack according to one embodiment of the present disclosure.

For example, the at least one insulator film 18 includes two sets of two different insulator films 18A, 18B, as shown in FIGS. 4-6. The two sets of two insulator films 18A, 18B may be deposited in an order: A, B, B, A. It will be appreciated that the two insulator films 18A, 18B may be such that the A insulator films are composed of silicon nitride and the B insulator films are composed of silicon dioxide to name a couple of non-limiting examples.

The MEMS die 12 includes at least one electrode 22 in contact with the sensor material 14. In the embodiments shown the electrodes 22 are disposed around the periphery of the sensor material 14. For example, the electrodes 22 may be in contact on opposing sides of the sensor material 14 in order to send an electrical signal across the sensing material from one side to an opposing side. It will be appreciated that the at least one electrode 22 may be composed of gold, or aluminum to name a couple of non-limiting examples The MEMS die 12 further includes a temperature sensor 24 disposed around the sensor material 14. The temperature sensor 24 is configured to monitor the temperature of the sensor material 14 in order to maintain a constant sensor material 14 temperature in any environment. In the embodiment shown in FIG. 2, the temperature sensor 24 is circumferentially disposed around the sensor material 14.

It will be appreciated that the temperature sensor 24 may be circumferential to, and/or underneath the electrodes 22 and sensor material 14. It will be further appreciated that the temperature sensor 24 may be disposed on or between any of the at least one insulator film 18, or on a bottom surface of the thermally conductive substrate 16. It may be further appreciated that the temperature sensor 24 may be enclosed by combinations of the at least one insulator film 18. Enclosing the temperature sensor 24 may prevent electromigration or corrosion of the temperature sensor 24 material. For example, enclosing the temperature sensor material 24 with a silicon dioxide film may also prevent silicide formation.

In the embodiment shown in FIG. 3, the temperature sensor 24 is shown surrounding three sides of the sensor material 14; thus, not crossing over the at least one electrode 22 or heater 26. It will be appreciated that the temperature sensor 24 may be composed of platinum or nickel to name a couple of non-limiting examples and contain a corrosion prevention coating.

The MEMS die 12 further includes a heater 26 circumferentially disposed around the sensor material 14, and temperature sensor 24. The heater 26 operates as a hot plate which controls the temperature of the sensor material 14 by applying a current through the heater 26. In an embodiment, the heater 26 includes a line width dimension, wherein the linewidth dimension is less than or equal to approximately 100 micrometers. It may also be appreciated that the linewidth of the heater 26 may be continuously varied to dissipate more or less power to heat the conductive substrate 16. It will also be appreciated that the heater 26 may be composed of platinum and nickel to name a couple of non-limiting examples, and contain a corrosion prevention coating.

In some embodiments, there is no cross-over or intersection between the heater 26, temperature sensor 24 and the at least one electrode 22. For example, the heater 26 may be circumferential to, and/or underneath the electrodes 22 and sensor material 14. The heater 26 may also be disposed on or between any of the at least one insulator film 18, or a bottom surface of the thermally conductive substrate 16. The heater 26 may also be enclosed by combinations of the at least one insulator film 18. Enclosing the heater 26 may prevent electromigration or corrosion of the heater 26 material. For example, enclosing the heater material 26 with a silicon dioxide film may prevent silicide formation.

The at least one insulator film 18 may be deposited prior to formation of the at least one electrode 22, temperature sensor 24, and heater 26, and that the second set of insulator films may be deposited after the at least one electrode 22, temperature sensor 24, and heater 26 have been formed, so as to enclose portions of each of the at least one electrode 22, temperature sensor 24, and heater 26.

In an embodiment, as shown in FIGS. 1, 2, 3 and 5, the MEMS die 12 further includes at least one aperture 28 disposed within the at least one insulator film 18. The at least one aperture 28 forms a contact point with the thermally conductive substrate 16, and is configured to provide an insulation resistance verification of the at least one insulator film 18, and allows for testing and diagnostics of the MEMS die 12.

It should be noted that barrier metals or other diffusion barriers, as are known in the art, may be employed to prevent substantial co-diffusion of the temperature sensor 24 material into the heater 26 material where they contact each other, for example, in a bond pad 32 or in the least one aperture 28. Similarly, it should be noted that barrier metals or other diffusion barriers may be employed to prevent substantial co-diffusion of the temperature sensor 24 material or the heater 26 material or both into the silicon substrate and vice versa. An appropriate barrier metal or other diffusion barrier may also be employed to prevent electrode 22 material from diffusing into the sensor material 14 where they are in contact. This may prevent undesirable shifts in the operating properties of the sensor material 14 over time, including stability, sensitivity or reaction time.

In another embodiment, MEMS die 12 further includes at least one passive heat exchanger 30 operably coupled to at least one bond pad 32, the at least one bond pad 32 is disposed on the at least one insulator film surface 18. In one embodiment, the at least one passive heat exchanger 30 is located on a periphery of the at least one insulator film surface 18. In an embodiment, the at least one passive heat exchanger 30 and the at least one bond pad 32 are disposed within the aperture 28. It will be appreciated that the at least one passive heat exchanger 30 may be coupled to the at least one bond pad 32 by any means known in the art, for example wire bonding, foil bonding, bump and flip chip to name a few non-limiting examples.

For example, the at least one passive heat exchanger 30 may be a wire bond configured to provide a connection means of electrical input and output to at least the electrode 22, detector 24, heater 26, and aperture 28. It will be appreciated that the at least one passive heat exchanger 30 is part of a thermal isolation scheme to exchange heat between the MEMS die 12 and a gas detector package/environment, and include small diameters and long lengths to reduce the rate at which heat is transferred. It will be further appreciated that in the embodiment shown in FIG. 3, the heater 26 substantially surrounds bond pads 32 such that there is no direct thermal path between the bond pads 32 and the sensor material 14.

In some embodiments, the passive heat exchangers 30 are coupled to place the MEMS die 12 in a spider die (i.e. floating die) configuration; however, it will be appreciated that the sensor material 14 on the MEMS die 12 may be substantially thermally isolated from its mounting by a number of configurations, such as a membrane isolating a central heated mass, tethers isolating a central heated mass, a diaphragm or perforated diaphragm isolating a central mass, a cantilevered mounting, etc. to name a few non-limiting examples. It will further be appreciated that the MEMS die 12 may be mounted to a plastic, ceramic, or TO packages to name a few non-limiting examples.

It will therefore be appreciated that the present embodiments include a MEMS die 12 including a heater 26 circumferentially disposed around a sensing material 14 to provide a more uniform heating to maximize the area available for detection.

While the invention has been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed is:

1. A microelectromechanical systems die comprising:
    a thermally conductive substrate;
    at least one insulator film disposed on the thermally conductive substrate;
    a sensor material that detects a presence of a gas as the gas passes over the sensor material, wherein the sensor material is disposed on the at least one insulator film;
    at least one electrode in contact with the sensor material;
    a heater; and
    a temperature sensor located between the heater and the sensor material, wherein the heater is circumferentially disposed around the sensor material and the temperature sensor, wherein the temperature sensor surrounds only three sides of the sensor material such that the temperature sensor does not cross over the at least one electrode or the heater.

2. The microelectromechanical systems die of claim 1, wherein the thermally conductive substrate is composed of silicon.

3. The microelectromechanical systems die of claim 1, wherein the sensor material is substantially centered on the at least one insulator film.

4. The microelectromechanical systems die of claim 1, further comprising:
    at least one bond pad disposed on the at least one insulator film; and
    at least one passive heat exchanger operably coupled to the at least one bond pad.

5. The microelectromechanical systems die of claim 4, wherein the heater substantially surrounds the at least one bond pad such that there is no direct thermal path between the at least one bond pad and the sensor material.

6. The microelectromechanical systems die of claim 4, wherein the heater is positioned such that there is no direct thermal path between the at least one bond pad and the sensor material.

7. The microelectromechanical systems die of claim 4, wherein the at least one passive heat exchanger is located on the periphery of the at least one insulator film.

8. The microelectromechanical systems die of claim 4, wherein the at least one passive heat exchanger comprises wire bonds.

9. The microelectromechanical systems die of claim 1, wherein the at least one insulator film encloses the temperature sensor and the heater.

10. The microelectromechanical systems die of claim 1 further comprising a diffusion barrier constructed and arranged to prevent diffusion between the at least one electrode and the sensor material.

11. The microelectromechanical systems die of claim 1 further comprising a diffusion barrier constructed and arranged to prevent diffusion between at least one of the at least one electrode, the temperature sensor, and the heater and the thermally conductive substrate.

12. The microelectromechanical systems die of claim 1, wherein the heater includes a linewidth dimension.

13. The microelectromechanical systems die of claim 12, wherein the linewidth dimension is less than or equal to approximately 100 micrometers.

14. The microelectromechanical systems die of claim 1 further comprising an aperture formed in the at least one insulator film to provide a contact point for testing the microelectromechanical systems die.

15. A gas detector package comprising:
    a microelectromechanical systems die comprising:
        a thermally conductive substrate;
        at least one insulator film disposed on the thermally conductive substrate;
        a sensor material that detects a presence of a gas as the gas passes over the sensor material, wherein the sensor material is disposed on the at least one insulator film;
        at least one electrode in contact with the sensor material;
        a heater; and
        a temperature sensor located between the heater and the sensor material, wherein the heater is circumferentially disposed around the sensor material and the temperature sensor, wherein the temperature sensor surrounds only three sides of the sensor material such that the temperature sensor does not cross over the at least one electrode or the heater.

16. The gas detector package of claim 15, wherein the thermally conductive substrate is composed of silicon.

17. The gas detector package of claim 15, wherein the sensor material is located substantially centered on the sensing surface.

18. The gas detector package of claim 15, further comprising:
    at least one bond pad disposed on the at least one insulator film; and
    at least one passive heat exchanger operably coupled to the at least one bond pad.

19. The gas detector package of claim 18, wherein the heater substantially surrounds the at least one bond pad such that there is no direct thermal path between the at least one bond pad and the sensor material.

20. The gas detector package of claim 18, wherein the heater is positioned such that there is no direct thermal path between the at least one bond pad and the sensor material.

21. The gas detector package of claim 18, wherein the at least one passive heat exchanger is located on the periphery of the at least one insulator film.

22. The gas detector package of claim 15, wherein the at least one insulator film encloses the temperature sensor and the heater.

23. The gas detector package of claim 15 further comprising a diffusion barrier constructed and arranged to prevent diffusion between the at least one electrode and the sensor material.

24. The gas detector package of claim 15 further comprising a diffusion barrier constructed and arranged to prevent diffusion between at least one of the at least one electrode, the temperature sensor, and the heater and the thermally conductive substrate.

25. The gas detector package of claim 15, wherein the heater includes a linewidth dimension.

26. The gas detector package of claim 25, wherein the linewidth dimension is less than or equal to approximately 100 micrometers.

27. The gas detector package of claim 15 further comprising an aperture formed in the at least one insulator film to provide a contact point for testing the microelectromechanical systems die.

\* \* \* \* \*